(12) United States Patent
Richards et al.

(10) Patent No.: US 8,102,879 B2
(45) Date of Patent: Jan. 24, 2012

(54) APPLICATION LAYER METRICS MONITORING

(75) Inventors: Christopher Richards, Ottawa (CA); Rob Cameron, Ottawa (CA); Jerry Mizell, Plano, TX (US)

(73) Assignee: Avaya Inc., Basking Ridge, NJ (US)

( * ) Notice: Subject to any disclaimer, the term of this patent is extended or adjusted under 35 U.S.C. 154(b) by 802 days.

(21) Appl. No.: 11/535,208

(22) Filed: Sep. 26, 2006

(65) Prior Publication Data

US 2007/0086336 A1  Apr. 19, 2007

Related U.S. Application Data

(60) Provisional application No. 60/721,808, filed on Sep. 29, 2005.

(51) Int. Cl.
*H04J 3/16* (2006.01)
(52) U.S. Cl. .................................................. 370/469
(58) Field of Classification Search .................. 709/224, 709/220, 223, 226; 370/229, 230, 230.1, 370/231, 233, 234, 236, 235, 252, 253, 468, 370/471, 401, 400, 465, 395.41, 469, 467, 370/466, 473, 485
See application file for complete search history.

(56) References Cited

U.S. PATENT DOCUMENTS

| | | | |
|---|---|---|---|
| 7,257,833 B1 * | 8/2007 | Parekh et al. | 726/1 |
| 7,433,943 B1 * | 10/2008 | Ford | 709/223 |
| 7,797,276 B1 * | 9/2010 | Yang | 707/636 |
| 2003/0229624 A1 * | 12/2003 | Petrisor et al. | 707/3 |
| 2004/0162901 A1 | 8/2004 | Mangipudi et al. | |
| 2005/0163047 A1 | 7/2005 | McGregor et al. | |
| 2006/0123479 A1 | 6/2006 | Kumar et al. | |
| 2006/0179296 A1 | 8/2006 | Bartlett et al. | |
| 2007/0156919 A1 * | 7/2007 | Potti et al. | 709/238 |

OTHER PUBLICATIONS

International Search Report for PCT/IB2006/002674 mailed Jun. 27, 2007.

* cited by examiner

*Primary Examiner* — Chi Pham
*Assistant Examiner* — Alexander Boakye
(74) *Attorney, Agent, or Firm* — Withrow & Terranova, PLLC

(57) ABSTRACT

The present invention enables the monitoring of application layer metrics of data packets for subscribers or groups of subscribers. In one embodiment, an edge routing node, such as an edge router or the like, between an access network and a core network will identify a subscriber associated with the incoming data packets and then identify an application layer policy to apply to the data packets. The application layer policy may identify the application layer metrics to monitor, how to analyze the application layer metrics, and perhaps actions to take in light of identifying certain application layer metrics, as well as identifying how, where, and when to report the application layer metrics, or an aggregation thereof. With the present invention, application layer metrics can be obtained and analyzed in real time on a subscriber-by-subscriber basis.

35 Claims, 3 Drawing Sheets

APPLICATION LAYER METRICS MONITORING

This application claims the benefit of U.S. provisional application Ser. No. 60/721,808 filed Sep. 29, 2005, the disclosure of which is incorporated herein by reference in its entirety.

FIELD OF THE INVENTION

The present invention relates to communications, and in particular to monitoring application layer metrics from data traffic of subscribers.

BACKGROUND OF THE INVENTION

Network operators of packet networks have traditionally struggled with monitoring the activity of their subscribers. The nature of packet communication makes controlling and allocating bandwidth among subscribers difficult. Since these networks have finite capacity, resource usage must be monitored to ensure that subscribers are allocated the resources to which they are entitled, and prevent subscribers from using more resources than they are entitled to. Traffic monitoring also allows network operators to detect overall usage patterns, changes in usage patterns, and the like, which aid in managing the packet networks. Such monitoring is generally focused on overall network traffic.

Although the resulting metrics of traditional monitoring are useful, the metrics provide little insight into how subscribers are actually using their allocated bandwidth. Without such knowledge, network operators have less information to aid them in configuring the networks to meet the current and future demands of the subscribers, as well as identify subscribers that are abusing communication privileges. Further, metrics for actual subscriber use could be passed on to service providers who provide services over the packet networks for the subscribers of the network providers. Various metrics related to the type and content of subscriber traffic could lead to enhanced services for the subscribers.

Unfortunately, there is no effective way to collect subscriber usage metrics on an application level. Although current techniques can monitor the physical, datalink, network, and transport layers of the Open Systems Interconnect Reference Model for a computer network (OSI LAYER 1-4), a breakdown of application use on a subscriber-by-subscriber basis is not available. Further, there is no way to monitor traffic content to aid in the analysis of the subscriber traffic. Accordingly, there is a need for an effective and efficient technique to gather and analyze detailed metrics for subscribers at an application layer level.

SUMMARY OF THE INVENTION

The present invention enables the monitoring of application layer metrics of data packets for subscribers or groups of subscribers. An application layer is one that corresponds to layer 7 of the OSI model. In one embodiment, an edge routing node, such as an edge router or the like, between an access network and a core network will identify a subscriber associated with the incoming data packets and then identify an application layer policy to apply to the data packets. The application layer policy may identify the application layer metrics to monitor, how to analyze the application layer metrics, and perhaps actions to take in light of identifying certain application layer metrics, as well as identifying how, where, and when to report the application layer metrics, or an aggregation thereof. With the present invention, application layer metrics can be obtained and analyzed in real time on a subscriber-by-subscriber basis.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS FIGURES

The accompanying drawing figures incorporated in and forming a part of this specification illustrate several aspects of the invention, and together with the description serve to explain the principles of the invention.

DETAILED DESCRIPTION OF THE PREFERRED EMBODIMENT

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention enables the monitoring of application layer metrics of data packets for subscribers or groups of subscribers. An application layer is one that corresponds to layer 7 of the OSI model. In one embodiment, an edge routing node, such as an edge router or the like, between an access network and a core network will identify a subscriber associated with the incoming data packets and then identify an application layer policy to apply to the data packets. The application layer policy may identify the application layer metrics to monitor, how to analyze the application layer metrics, and perhaps actions to take in light of identifying certain application layer metrics, as well as identifying how, where, and when to report the application layer metrics, or an aggregation thereof. With the present invention, application layer metrics can be obtained and analyzed in real time on a subscriber-by-subscriber basis.

Figure 1:
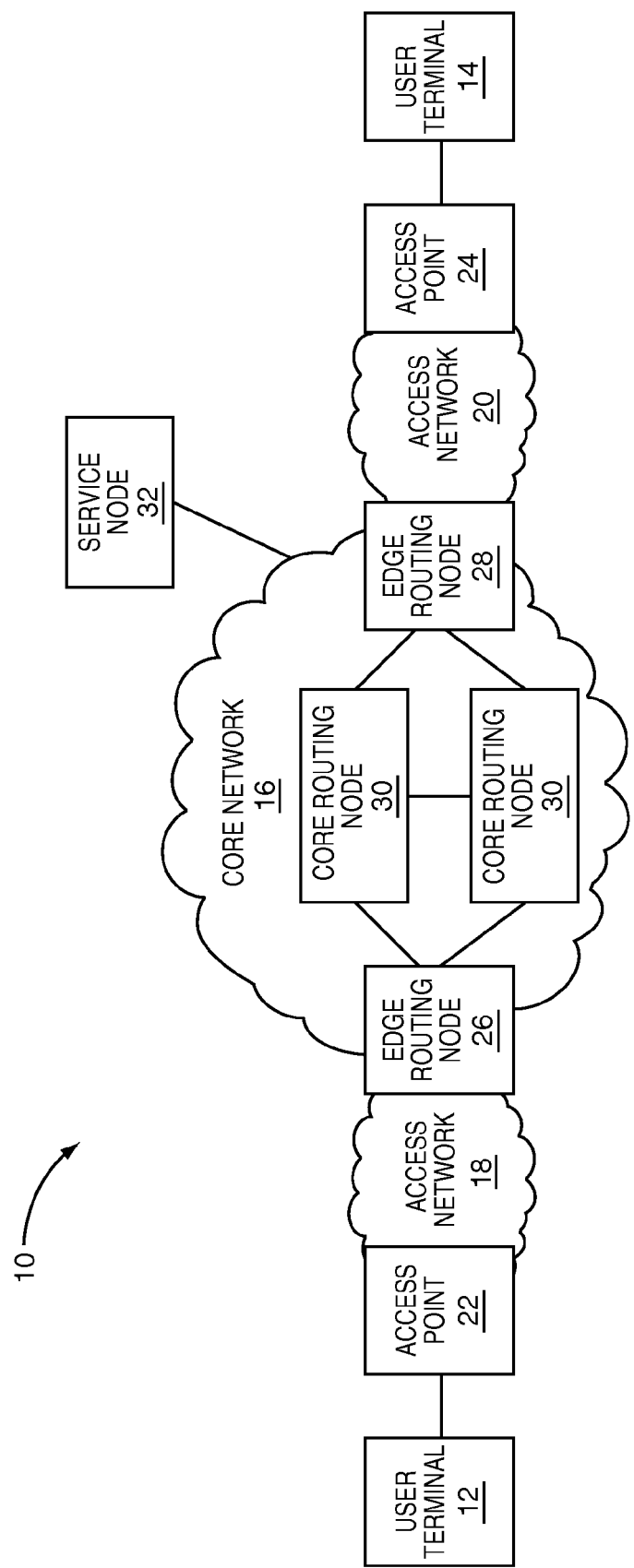
FIG. 1 is a block representation of a communication environment according to one embodiment of the present invention.

Prior to delving into the details of the present invention, an overview of a communication environment 10 in which the present invention may be employed is provided in association with FIG. 1. The communication environment 10 allows user terminals 12 and 14 of different subscribers to communicate with one another via a core network 16, which supports packet-based communications. Access to the core network 16 by the user terminals 12, 14 is provided by the access networks 18 and 20, respectively. The user terminal 12 may gain access to the access network 18 through an appropriate access point 22, whereas user terminal 14 may gain access to the access network 20 via an access point 24. The access network 18 is coupled to the core network 16 via an edge routing node 26, while the access network 20 is coupled to the core network 16 via an edge routing node 28. Routing through the core network 16 between the edge routing nodes 26 and 28 may be provided by any number of core routing nodes 30, which are distributed throughout the core network 16.

The edge routing nodes 26 and 28 may be multiple service edge devices, which are capable of facilitating different types of communication sessions for various types of applications supported by the user terminals 12, 14. The user terminals 12, 14 may be any type of fixed or mobile terminal, such as cellular telephones, personal digital assistants, personal computers, gaming consoles, Internet Protocol (IP) based telephone terminals, and the like. Accordingly, the access points 22, 24 and the corresponding access network 18, 20 may take various forms and may represent cable access networks, telephone access network, digital subscriber line access networks, cellular access networks, and wired or wireless local area networks. The edge routing nodes 26 and 28 will be able to provide the interworking between the access techniques employed to serve the user terminals 12 and 14 and the communication technique employed by the core network 16.

In operation, the edge routing nodes 26 and 28 receive data traffic either from a user terminal 12, 14 via the access network 18, 20, for forwarding over the core network 16 toward the destination, or receive data traffic from the core network 16 for delivery to the user terminal 12, 14 over the appropriate access network 18, 20. As the data traffic enters the edge routing node 26, 28, traffic is inspected in the data plane as opposed to the control plane, and application layer metrics are collected based on the data packets of the data traffic. The inspection may be provided without affecting the routing of the data traffic toward the appropriate destination. The application layer metrics that are collected may be reported to an appropriate management service for analysis. As illustrated in FIG. 1, the management service is provided by a service node 32.

The application layer metrics are those metrics that are dependant on the particular application or type of application with which the data traffic is associated. In other words, the data traffic is part of a communication session associated with that application or a particular type of application. The data traffic, and the data packets thereof, have application layer metrics that are a function of the application or type of application with which the communication session is associated. Application types may include file transfer, instant messaging, email, streaming audio, streaming video, voice, short message service messages, text messages, web applications, and the like.

In one embodiment of the present invention, application layer policies are defined for a given user or group of users. The application layer policy may identify what data packets or types of data packet to analyze, the information to analyze within the data packets, how to analyze information to be analyzed, as well as actions to take in response to certain conditions, which are determined in light of the information analyzed. In general, one or more subscribers will be associated with an application layer policy. As such, invocation of an application layer policy is triggered based on a source or destination address of the data packet. Once the source or destination is identified for a data packet, any application layer policies for the corresponding subscriber are identified and implemented for the data packet or the associated data traffic.

Figure 2:
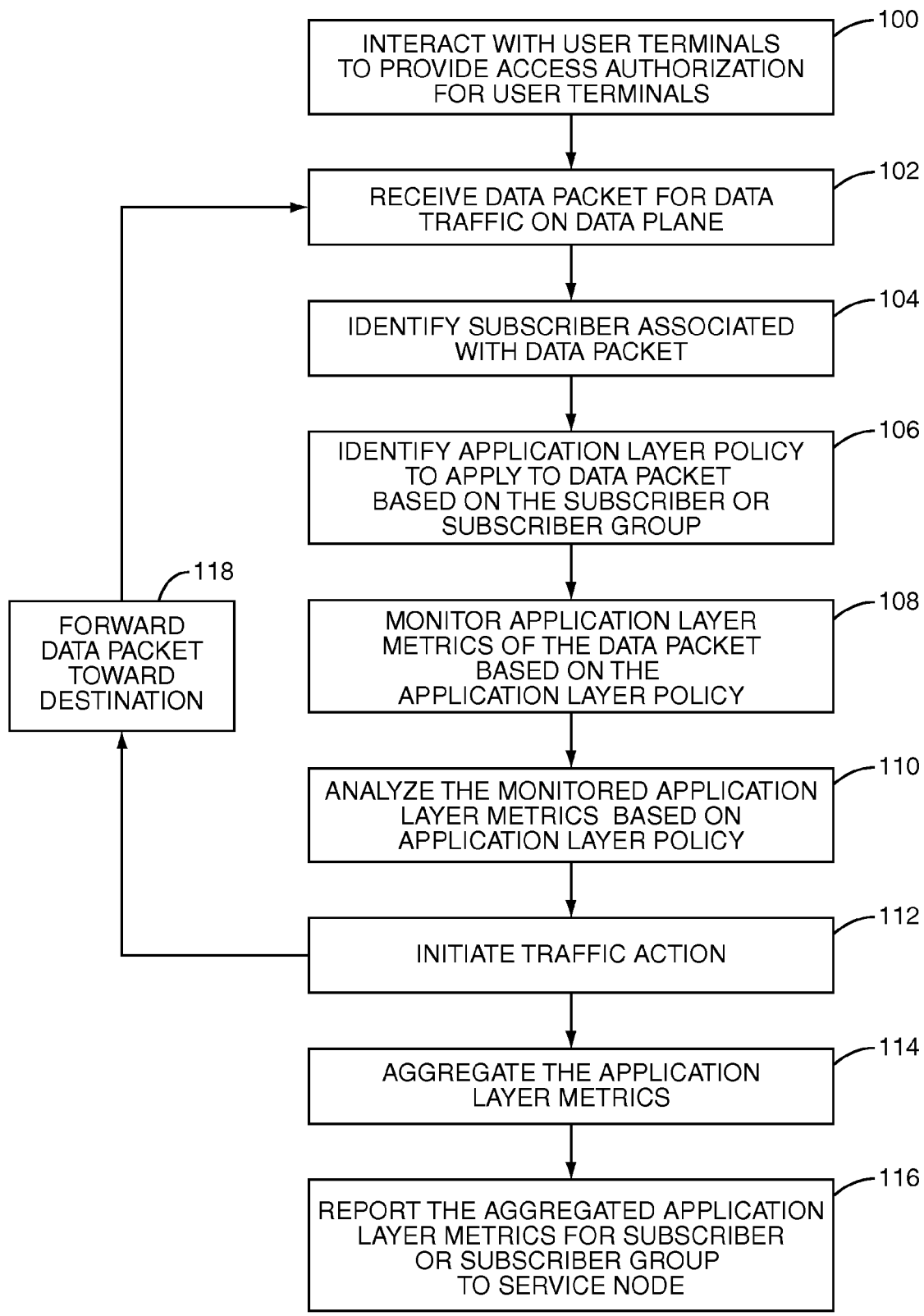
FIG. 2 is a flow diagram illustrating operation of one embodiment of the present invention.

Turning now to FIG. 2, a flow diagram is provided to illustrate operation of the present invention according to one embodiment. Initially, the edge routing nodes 26, 28 may interact with the user terminals 12, 14 to provide access authorization for the user terminals 12, 14 to communicate over the core network 16 (step 100). Authorization is generally a control plane function. The following steps may be provided as a data plane function. Once authorized, the edge routing nodes 26, 28 will begin receiving and routing data packets to facilitate communications over the core network 16 and the respective access networks 18 and 20. For this example, operation of the edge routing node 26 is described; however, those skilled in the art will recognize that the edge routing node 28 will operate in a similar fashion.

In operation, the edge routing node 26 will receive a data packet for data traffic on the data plane (step 102), and identify the subscriber associated with the data packet (step 104). Identification of the subscriber may be based on identifying the source or destination of the data packet or other information provided in the header of the packet, which corresponds to the subscriber or user terminal 12 associated with the subscriber. For data packets received from the access network 18, the edge routing node 26 may also analyze port, interface, and session identification information to associate the data packet with a subscriber. For the purposes of discussion, the term "subscriber information" is used in a broad fashion to represent any type of information that may be used to identify or associate an application layer policy with a particular subscriber or group of subscribers. As such, the application layer policy may be associated with a particular identifier or address associated with the user terminal 12. Therefore, identification of the subscriber may simply be identifying the address or identifier of the user terminal 12.

Once the identity of the subscriber is determined from the data packet, an application layer policy to apply to the data packet, or subsequent data packets associated with the data packet, is identified based on the subscriber (step 106). Notably, an application layer policy may be provided for a group of subscribers. Regardless of whether an application layer policy is provided for an individual subscriber or group of subscribers, there must be a mechanism in place to identify the subscriber and then associate the subscriber with a particular application layer policy.

Based on the application layer policy, the edge routing node 26 will monitor application layer metrics of the data packet or subsequent data packets associated with the data packet (step 108), and analyze the monitored application layer metrics based on the application layer policy (step 110). Depending on the application layer metrics that were monitored and analyzed, the edge routing node 26 may initiate a traffic action on the data packet, as well as on subsequent data packets associated therewith based on the application layer policy (step 112). Further, the edge routing node 26 may aggregate the application layer metrics that are monitored (step 114) and report the aggregated application layer metrics for the subscriber or group of subscribers to the service node 32 (step 116). The service node 32 may employ various techniques to analyze and use the aggregated application layer metrics received from the edge routing node 26.

While the edge routing node 26 is monitoring and analyzing the data packets based on the application layer policy, the data packets are continuously forwarded toward their destinations over the associated access network 18 or the core network 16, unless the application layer policy dictates otherwise (step 118). Accordingly, the edge routing node 26 remains a routing device and continuously receives and forwards data packets. During this routing operation, the edge routing node 26 will identify an application layer policy to apply to the data packet or the data traffic associated with the data packet. The application layer policy will identify the application layer metrics to monitor as well as how the application layer metrics should be monitored and reported, if necessary, to an appropriate service node 32. A unique aspect of the present invention is the ability for the edge routing nodes 26, 28 to monitor data packets based on application layer metrics for individual subscribers or defined groups of subscribers. As such, metrics may be gathered and analyzed in light of a given subscriber's use of an application or type of application.

With the present invention, application layer policies may be established to identify how many emails a particular user is sending and provide an alarm or appropriate information after a certain number of emails have been sent in total or over a certain period of time. Application layer metrics may be gathered to identify the most popular web destinations for a particular subscriber or group of subscribers. The application layer metrics that are monitored may include the actual data content of the data packets. As such, application layer metrics may be obtained to identify the most popular web searches made by a particular subscriber or group of subscribers. The content may be used to identify particular application or type of application associated with the data packet.

Notably, not all of the data packets for a given communication session need to be monitored or analyzed. For example, once one or more data packets for a given communication session have been analyzed to identify the session, the application, or application type associated with the communication session, and any pertinent information related thereto, the remaining data packets may or may not need to be analyzed, depending on the application layer policy. Those skilled in the art will recognize various techniques for monitoring application layer metrics for a subscriber or group of subscribers based on an application layer policy.

In addition to reporting the raw application layer metrics or aggregated application layer metrics, the application layer policy may dictate certain actions to be taken by the edge routing nodes 26, 28. For example, the actions that may be taken may include sending certain reports to the service node 32, the user terminals 12, 14, or other entities associated with the communication session, or the application layer policies may dictate more drastic actions, such as blocking communication sessions or dropping the data packets if the application layer metrics meet certain conditions or indicate certain events have occurred.

Figure 3:
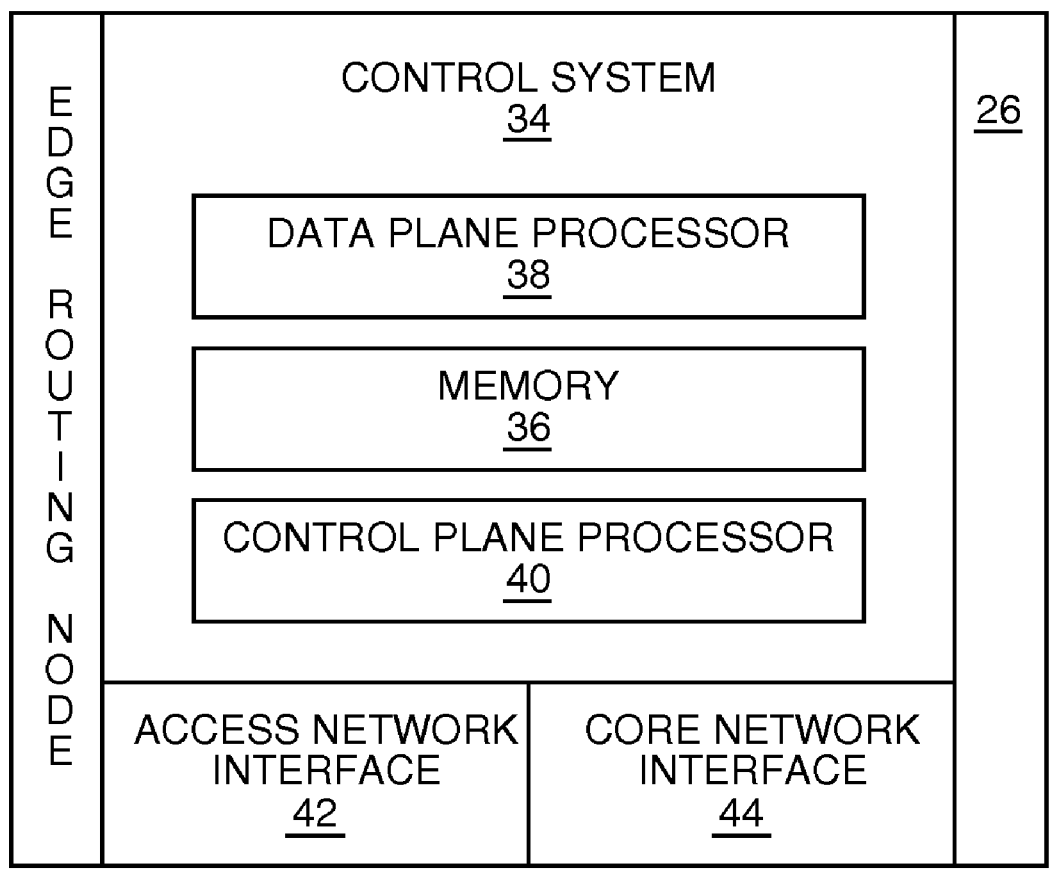
FIG. 3 is a block representation of an edge routing node according to one embodiment of the present invention.

Turning now to FIG. 3, a block representation of an edge routing node 26 is provided. The edge routing node 26 may include a control system 34 having memory 36, a data plane processor 38, and a control plane processor 40. The data plane processor 38 operates at the data plane and functions to route and process data packets, which represent those packets carrying content for a particular communication session. The control plane processor 40 processes control packets, which generally do not carry content associated with the session, but instead carry information used to establish, control, and break down communication sessions in which the data traffic is carried. The control system 34 is associated with an access network interface 42 to facilitate communications over the access network 18, and a core network interface 44 to facilitate communications over the core network 16.

Although the functionality of the present invention has been illustrated as being employed in an edge routing node 26, the concepts of the present invention may be employed in various networking devices at different locations throughout the access networks 18, 20 as well as the core network 16.

Those skilled in the art will recognize improvements and modifications to the preferred embodiments of the present invention. All such improvements and modifications are considered within the scope of the concepts disclosed herein and the claims that follow.

What is claimed is:

1. A method comprising:
   identifying a subscriber associated with data traffic;
   identifying, in an edge routing device, an application layer policy for the subscriber;
   monitoring, in the edge routing device, application layer metrics of the data traffic of the subscriber based on the application layer policy; and
   determining from the application layer metrics at least one web search for the subscriber.

2. The method of claim 1 wherein the application layer metrics comprise metrics to identify an application associated with the data traffic.

3. The method of claim 1 wherein the application layer metrics comprise metrics to identify a type of application associated with the data traffic.

4. The method of claim 1 wherein the application layer metrics comprise data content of at least one data packet of the data traffic.

5. The method of claim 1 further comprising analyzing the application layer metrics based on the application layer policy to create an application layer metrics analysis.

6. The method of claim 1 further comprising aggregating the application layer metrics based on the application layer policy to create an application layer metrics analysis.

7. The method of claim 1 further comprising reporting to a service node at least one of the group consisting of the application layer metrics, an analysis of the application layer metrics, and an aggregation of the application layer metrics.

8. The method of claim 1 further comprising:
   identifying a plurality of subscribers associated with data traffic; and
   monitoring application layer metrics of the data traffic of the plurality of subscribers based on the application layer policy.

9. The method of claim 8 further comprising reporting to a service node at least one of the group consisting of the application layer metrics, an analysis of the application layer metrics, and an aggregation of the application layer metrics for the plurality of subscribers, which includes the subscriber.

10. The method of claim 1 wherein identifying the subscriber comprises identifying at least one of the group consisting of a source, destination, session, port, and address associated with the data traffic of the subscriber.

11. The method of claim 1 further comprising effecting an action other than routing on at least one data packet of the data traffic based on the application layer policy.

12. The method of claim 1 further comprising receiving data packets of the data traffic from a first network and routing the data packets toward a destination over a second network.

13. An edge routing device comprising:
   an access network interface;
   a core network interface; and
   a data plane processor associated with the access network interface and the core network interface and adapted to:
      identify a subscriber associated with data traffic;
      identify an application layer policy for the subscriber;
      monitor application layer metrics of the data traffic of the subscriber based on the application layer policy; and
      determine from the application layer metrics at least one web search for the subscriber.

14. The edge routing device of claim 13 wherein the application layer metrics comprise metrics to identify an application associated with the data traffic.

15. The edge routing device of claim 13 wherein the application layer metrics comprise metrics to identify a type of application associated with the data traffic.

16. The edge routing device of claim 13 wherein the application layer metrics comprise data content of at least one data packet of the data traffic.

17. The edge routing device of claim 13 wherein the data plane processor is further adapted to analyze the application layer metrics based on the application layer policy to create an application layer metrics analysis.

18. The edge routing device of claim 13 wherein the data plane processor is further adapted to aggregate the application layer metrics based on the application layer policy to create an application layer metrics analysis.

19. The edge routing device of claim 13 wherein the data plane processor is further adapted to report to a service node at least one of the group consisting of the application layer metrics, an analysis of the application layer metrics, and an aggregation of the application layer metrics.

20. The edge routing device of claim 13 wherein the data plane processor is further adapted to:
   identify a plurality of subscribers associated with data traffic; and
   monitor application layer metrics of the data traffic of the plurality of subscribers based on the application layer policy.

21. The edge routing device of claim 20 wherein the data plane processor is further adapted to report to a service node at least one of the group consisting of the application layer metrics, an analysis of the application layer metrics, and an aggregation of the application layer metrics for the plurality of subscribers, which includes the subscriber.

22. The edge routing device of claim 13 wherein to identify the subscriber, the data plane processor is further adapted to identify at least one of the group consisting of a source, destination, session, port, and address associated with the data traffic of the subscriber.

23. The edge routing device of claim 13 wherein the data plane processor is further adapted to effect an action other than routing on at least one data packet of the data traffic based on the application layer policy.

24. The edge routing device of claim 13 wherein the data plane processor is further adapted to receive data packets of the data traffic from a first network and route the data packets toward a destination over a second network.

25. The method of claim 1 wherein the method further comprises applying, in the edge routing device, the application layer policy of the subscriber to at least one data packet of the data traffic of the subscriber.

26. The method of claim 1 wherein the at least one web search for the subscriber comprises a popular web search for the subscriber.

27. The method of claim 1 wherein the method further comprises determining from the application layer metrics at least one web destination for the subscriber.

28. The method of claim 27 wherein the at least one web destination for the subscriber comprises at least one popular web destination for the subscriber.

29. The method of claim 1 wherein the method further comprises:
   determining from the application layer metrics a number of emails that the subscriber has sent during at least one time interval;
   determining that the number of emails that the subscriber has sent during the at least one time interval exceeds a threshold; and
   generating an alarm upon determining that the number of emails that the subscriber has sent during the at least one time interval exceeds the threshold.

30. The edge routing device of claim 13 wherein the data plane processor is further adapted to apply the application layer policy for the subscriber to at least one data packet of the data traffic of the subscriber.

31. The edge routing device of claim 13 wherein the at least one web search for the subscriber comprises a popular web search for the subscriber.

32. The edge routing device of claim 13 wherein the data plane processor is further adapted to determine from the application layer metrics at least one web destination for the subscriber.

33. The edge routing device of claim 32 wherein, wherein the at least one web destination for the subscriber comprises at least one popular web destination for the subscriber.

34. The edge routing device of claim 13 wherein the data plane processor is further adapted to:
   determine from the application layer metrics a number of emails that the subscriber has sent during at least one time interval;
   determine that the number of emails that the subscriber has sent during the at least one time interval exceeds a threshold; and
   generate an alarm upon determining that the number of emails that the subscriber has sent during the at least one time interval exceeds the threshold.

35. A method comprising:
   identifying a subscriber associated with data traffic;
   identifying, in an edge routing device, an application layer policy for the subscriber;
   monitoring, in the edge routing device, application layer metrics of the data traffic of the subscriber based on the application layer policy; and
   reporting to a service node at least one of the group consisting of the application layer metrics, an analysis of the application layer metrics, and an aggregation of the application layer metrics.

* * * * *